United States Patent [19]

Muller

[11] Patent Number: 5,714,162
[45] Date of Patent: Feb. 3, 1998

[54] SCOPOLAMINE PATCH

[75] Inventor: Walter Muller, Neuwied, Germany

[73] Assignee: LTS Lohmann Therapie-Systeme GmbH & Co. KG, Neuwied, Germany

[21] Appl. No.: 369,019

[22] Filed: Jan. 5, 1995

[30] Foreign Application Priority Data

Sep. 16, 1994 [DE] Germany .............. 44 33 004.9
Oct. 31, 1994 [DE] Germany .............. 44 38 989.2

[51] Int. Cl.$^6$ .............................................. A61F 13/02
[52] U.S. Cl. .................................. 424/448; 424/449
[58] Field of Search .............................. 424/448, 449

[56] References Cited

U.S. PATENT DOCUMENTS 5,032,403  7/1991  Sinnreich ..................... 424/448
5,176,917  1/1993  Muller ......................... 424/448
5,310,559  5/1994  Shah ........................... 424/448
5,474,783  12/1995  Miranda ...................... 424/448

*Primary Examiner*—D. Gabrielle Phelan
*Attorney, Agent, or Firm*—Sprung Kramer Schaefer & Briscoe

[57] ABSTRACT

A scopolamine-containing transdermal therapeutic system in the form of a patch is described whose active substance-containing layers comprise as base polymer copolymers of acrylic acid or methacrylic acid derivatives and scopolamine base in a concentration corresponding to 50–100% of the saturation solubility, preferably 60–100% of the saturation solubility, in the total vehicle formulation.

11 Claims, 2 Drawing Sheets

SCOPOLAMINE PATCH

Scopolamine is a known substance which is administered transdermally with systemic action in a marketed plaster system. Scopolamine is a so-called antiemitic, it is preferably used to avoid nausea and vomiting, for example, arising from repeated passive changes in the balance occurring during traveling.

The therapeutic advantage of the transdermal administration is the fact that the active substance supply is effected slowly and in a controlled manner through the transdermal system. Thereby it is possible to hit the relatively narrow therapeutic window of scopolamine reliably and, on the one hand, to achieve therapeutically effective plasma levels without having to fear the side effects caused by an overdosage, on the other hand. The structure of the marketed system is described in U.S. Pat. No. 3,797,494. It mainly consists of a backing layer, an active substance reservoir, a microporous membrane, a skin adhesive layer which also comprises active substances, and a protective film which is to be removed prior to use. The reservoir and the skin adhesive layer are built up of a mixture of polyisobutylenes having different molecular weights and a mineral oil. The active substance is dispersed in said mixture as viscous liquid. A transdermal system whose active substance-containing components are built up on this basis has considerable disadvantages. Under certain conditions, spontaneous crystallizations occur which affect the bioavailability of the active substance in the patch.

U.S. Pat. No. 4,832,953 describes the details of this instability at full length. It describes a method of preventing crystallization by subsequent heat treatment of the already packaged patch. According to the statements in this patent, it is the scopolamine hydrate that crystallizes above all.

The fact that an active substance contained in an administration form—under certain conditions which can only hardly be defined—changes its state of aggregatation with a simultaneous influence on the bioavailablity at an unpredictable time after its production is a considerable disadvantage.

Starting from this state of the art, it is the object of the present invention to provide an alternative polymeric formulation for the active substance scopolamine base, which does not have the considerable disadvantages described in the above-mentioned patents.

In accordance with the present invention, there is provided a transdermal therapeutic system in the form of a patch having a layered structure, consisting of a backing layer, a pressure sensitive adhesive active substance reservoir, if needed a membrane controlling the active substance flux, optionally an additional skin adhesive layer, and a removable protective film, and comprising the active substance scopolamine base, wherein the active substance-containing layers of the patch comprise as base polymer copolymers of acrylic acid or methacrylic acid derivatives and scopolamine base in a concentration corresponding to 50–100% of the saturation solubility, preferably 60–100% of the saturation solubility in the total vehicle formulation.

Advantageously it is a matrix system or a membrane system wherein the membrane comprises a copolymer of ethylene and vinyl acetate, preferably at least 4% of vinyl acetate. Desirably the saturation solubility of the scopolamine base in the adhesive or in the adhesive/auxiliary agent mixture amounts to 10–30%-wt., and the active substance-containing layers of the patch comprise hydrocarbons, preferably dioctyl cyclohexane, to decrease the saturation solubility for scopolamine base, or fatty acids or fatty alcohols to increase the saturation solubility, preferably oleic acid and oleyl alcohol.

According to the literature, scopolamine base is a viscous liquid. However, it is difficult to understand for the expert that a relatively polar substance having a molecular weight of 303.35 shall be a liquid in its stable state of aggregation. Nevertheless, it is possible to crystallize scopolamine base under adequate conditions. A white solid matter having a melting point of about 68° C. is obtained. Hence it follows that the active substance is contained in the prior art patches in an unstable modification. Thus it is very likely that it is not the hydrate of the scopolamine base that crystallizes but that a liquid-solid phase transition of the scopolamine base itself occurs. Since liquid scopolamine base, as compared to crystalline scopolamine base, represents a modification having an increased energy content, it follows from the laws known to those skilled in the art that scopolamine base is dissolved in the polymer itself in a concentration exceeding the saturation concentration. Thus, crystallization cannot only take place in the dispersed portion of the active substance but also in the polymer itself.

The present invention advantageously provides a new formulation of the base polymers comprising the scopolamine, which avoids the known drawbacks with respect to the efficiency of the patch. The fact that according to the present invention polymers are used which comprise the active substance in completely dissolved form in concentrations below or—at best—equal to the saturation concentration advantageously avoids an instability of the active substance scopolamine and its crystallization in the patch. To this end, these polymers must have an increased solvency for scopolamine base as compared to the formulations known from the art. Self-adhesive copolymers based on polyacrylic acids and their derivatives have turned out to be suitable polymers. In such polymers scopolamine base has a solubility between about 10 and 20% (w/w), depending on the exact composition of the copolymers and on the amount and kind of the added auxiliary agents. This is more than sufficient to place in a patch which has a size of about 2.5 $cm^2$ and the normal thickness of transdermal systems the required active substance amount, e.g., for a three-day treatment for the prevention of travel sickness.

The properties of these polyacrylate adhesives with respect to adhesive power, cohesion, and solvency may be varied by the choice of the monomers used for their production and of the molecular weight which can be predetermined by the polymerization conditions. According to the present invention, the solvency for scopolamine base is primarily important. Since scopolamine base is a relatively polar substance, those polyacrylate adhesives are suitable that have polar functional groups. Examples of these groups usually present in polyacrylate adhesives include carboxyl groups, hydroxyl groups and amino groups. Adequate monomers which may serve to introduce these groups into the adhesive include, for example, methacrylic acid, acrylic acid, semi-esters of diols with acrylic acid and methacrylic acid, and esters of both acids with amino alcohols.

Polyacrylate adhesives are compatible with a variety of low-molecular substances. The addition of these substances may be used to modify the solvency of given polyacrylate adhesives in accordance with this compound. In practice this means that polyacrylate adhesives having an insufficient number of polar groups must be provided with an addition of relatively polar inactive ingredients, and that polyacrylate adhesives having an excessive number of polar groups must be provided with relatively non-polar inactive ingredients. Since the thermodynamic activity of active substances does not depend on the absolute concentration but on the ratio of the actual concentration to the saturation solubility, the latter possibility is important to save active substance in a polyacrylate adhesive having an excessive solubility for the active substance by reducing the solubility for scopolamine base. Seen from this aspects, a saturation solubility of scopolamine base in the adhesive or in the mixture adhesive/inactive ingredient of 10-30 percent by weight is to be regarded as the optimum according to the present invention.

Since scopolamine base is a relatively polar-substance, the addition of liquid hydrocarbons can particularly be used to lower the saturation solubility. Dioctyl cyclohexane has proved to be particularly suitable.

As more strongly polar substances to increase the saturation solubility fatty acids, fatty alcohols, polyethylene or polypropylene glycol, derivatives of glycerol, and pantothenyl alcohol may primarily be used. Fatty acids, such as oleic acid, have proved to be particularly suitable.

BRIEF DESCRIPTION OF THE DRAWINGS

The invention will be further described with reference to the tables which are set forth hereinbelow and the accompanying drawings, wherein.

Figure 1:
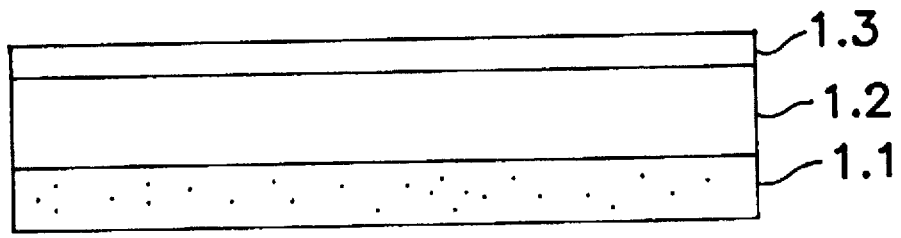
FIG. 1 is a schematic side view of a matrix system in accordance with the invention.
Figure 2:
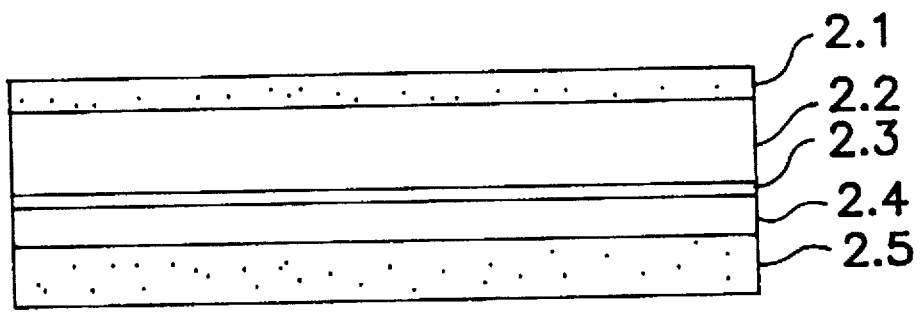
FIG. 2 is a schematic side view of a membrane system in accordance with the invention.

Referring now more particularly to the drawings, based on adhesives or adhesive/auxiliary agent formulations described hereinabove, both so-called transdermal matrix systems and membrane systems may be manufactured which have proved to be bioequivalent with the marketed competitive products in significant in-vitro-permeation experiments on human skin. The structure of such transdermal systems is shown in FIGS. 1 and 2.

The most simple transdermal system from the constructional point of view is a matrix system. It consists of a backing layer (1.3) which is substantially impermeable to the active substance and the auxiliary agents, an active substance-containing, self-adhesive polymeric formulation (1.2), and a protective film (1.1) which is to be removed prior to use. Materials suitable for the backing layer and the protective layer are known to the skilled artisan. Films based on polyethylene terephthalate can practically be used universally, with the protective film being additionally siliconized, at least on the side contacting the adhesive, in order to facilitate removal of the patch. In case the pressure sensitive adhesiveness of the polymeric formulation is too low, it may be provided with an additional pressure sensitive adhesive layer facing the skin (not shown here).

A membrane system consists of a backing layer (2.5), an active substance reservoir (2.4), the membrane (2.3), a skin contacting layer (2.2), and a protective layer (2.1) which is to be removed prior to use.

The active substance reservoir layer and the skin contacting layer may have the same or a different composition. The mere important fact according to the present is that at least the reservoir is based on a polyacrylate adhesive and has a solvency for scopolamine base between 10 and 30 percent by weight.

The materials suitable for a membrane are also known to those skilled in the art. Membranes based on copolymers of ethylene and Vinyl acetate have proved to be particularly suitable in combination with a polyacrylate adhesive according to the present invention. The active substance flow through this membrane may be controlled by the content of vinyl acetate and the thickness of the membrane. The higher the content of vinyl acetate and the less the thickness, the higher the permeablity of the membrane for scopolamine base. Membranes having a vinyl acetate content of at least 4% and a thickness between 50 and 100 μm have proved to be suitable. Membranes having a thickness of 50 μm and a vinyl acetate content of 9-20% have proved to be particularly suitable for a patch having a size not exceeding 5 cm$^2$.

Figure 3:
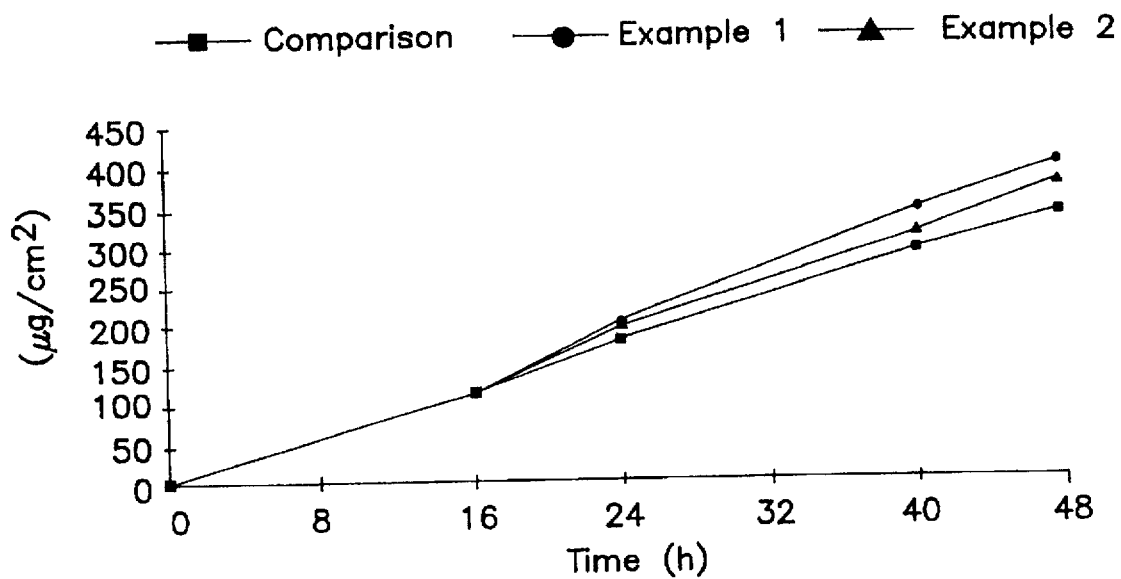
FIG. 3 is a diagram showing the results of Examples 1 and 2 alongside a comparison.

The results of permeation experiments using matrix systems according to the present invention are shown in Table 1 and FIG. 3. The tests were carried out using Franz' permeation cells and human skin (female breast skin of breast reduction operations).

Figure 4:
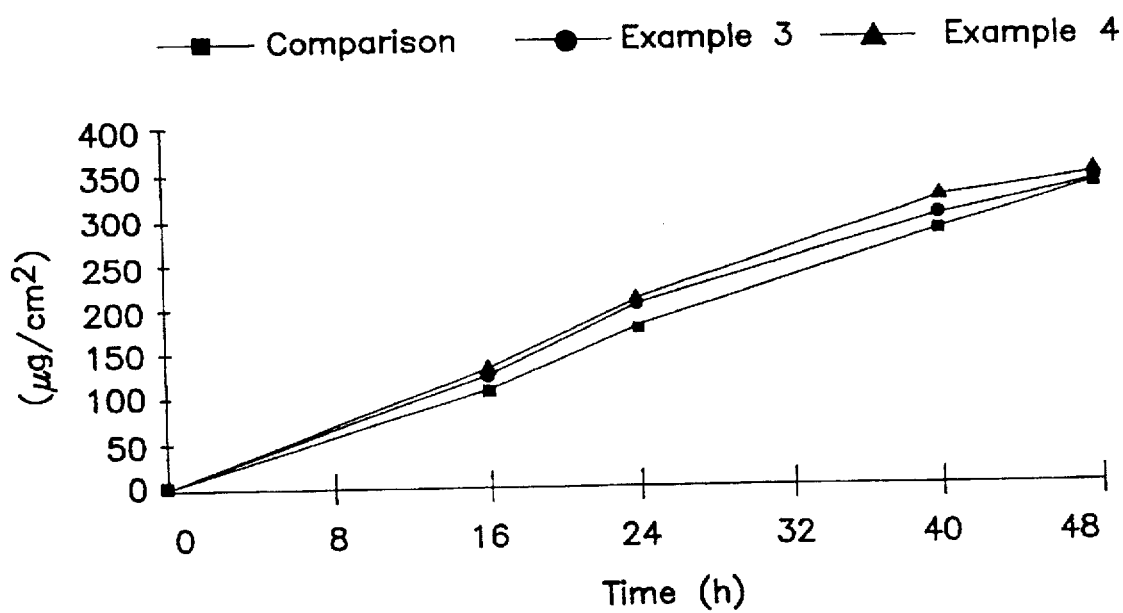
FIG. 4 is a similar diagram relating to Examples 3 and 4.

The results using membrane systems according to the present invention are shown in Table 2 and FIG. 4.

TABLE 1

Permeation measurements with matrix systems according to Example 1 and 2.

| Formulation | Accumulated amount of scopolamine base permeated through the skin given in μg/cm$^2$ (average value of n = 3) after | | | |
|---|---|---|---|---|
| | 16 h | 24 h | 40 h | 48 h |
| Comparison | 115.8 | 185.1 | 297.4 | 350.7 |
| Example 1 | 118.1 | 208.0 | 349.2 | 403.0 |
| Example 2 | 120.3 | 203.4 | 320.2 | 410.3 |

Table 2

Permeation measurements with membrane systems according to Examples 3 and 4

| Formulation | Accumulated amount of scopolamine base permeated through the skin given in μg/cm$^2$ (average value of n = 3) after | | | |
|---|---|---|---|---|
| | 16 h | 24 h | 40 h | 48 h |
| Comparison | 115.8 | 185.1 | 297.4 | 350.7 |
| Example 3 | 129.9 | 209.6 | 311.7 | 350.0 |
| Example 4 | 135.4 | 215.3 | 330.8 | 360.4 |

The results of these permeation experiments clearly show that patches according to the present invention have the same efficiency as the comparative samples, however, they do not have their disadvantages. Since the active substance concentration does not exceed the saturation solubility, there is no danger of recrystallization. Also, the formation of crystalline scopolamine hydrate is as good as impossible, since polyacrylate formulations—owing to their chemicophysical properties—have a solvency for scopolamine hydrate that is sufficient to prevent a recrystallization with the water amounts practically present in the adhesive.

EXAMPLES

Example 1

27 g polyacrylate adhesive (Durotak 901-1051, solids content 52%)

3.4 g oleic acid 0.12 g aluminum acetylacetonate 4.0 g scopolamine base and 3.7 g ethanol are mixed carefully and coated on a siliconized polyester film as a film of 200 μm thickness. The solvent-containing film is dried at 50° C. for 30 minutes and covered with a polyester film having a thickness of 23 μm. The individual patch systems (area: 2.5 cm²) are punched from the total laminate.

Example 2

27 g polyacrylate adhesive (Durotak 901-1051, solids content 52%)
3.4 g oleyl alcohol
0.12 g aluminum acetylacetonate
3.0 g scopolamine base
and 3.7 g ethanol are mixed carefully and coated on a siliconized polyester film as a film of 200 μm thickness. The solvent-containing film is dried at 50° C. for 30 minutes and covered with a polyester film having a thickness of 23 μm. The individual patch systems (area: 2.5 cm²) are punched from the complete laminate.

Example 3

73.6 g polyacrylate adhesive (Durotak 901-1051, solids content 52%)
9 g oleic acid
0.38 g aluminum acetylacetonate
12.0 g scopolamine base
and 17 g ethanol are mixed carefully and used for the coating processes.

a. Production of the skin adhesive layer

The mass is coated on a siliconized polyester film as a film of 50 μm thickness. The solvent-containing film is dried at 50° C. for 30 minutes and covered with a membrane having thickness of 50 μm and made of an ethylene-vinyl-acetate copolymer having a vinyl acetate content of 9%.

b. Production of the reservoir layer

The same mass is coated on another siliconized polyester film at a thickness of 150 μm in a second coating step; after removal of the solvents it is covered with a polyester film having a thickness of 23 μm.

c. Production of the total laminate

The reservoir layer manufactured according to b is peeled off the polyester film and laminated onto the membrane of the skin adhesive layer manufactured according to a.

The patch systems are punched from the total laminate at a size of 2.5 cm².

Example 4

73.6 g polyacrylate adhesive (Durotak 901-1051, solids content 52%)
9 g oleyl alcohol
0.38 g aluminum acetylacetonate
9.0 g scopolamine base
and 17 g ethanol are mixed carefully and used for the coating processes.

The further procedure corresponds to Example 3.

It is understood that the specification and examples are illustrative but not limitative of the present invention and that other embodiment within the spirit and scope of the invention will suggest themselves to those skilled in the art.

I claim:

1. A transdermal therapeutic system in the form of a patch containing scopolamine base and having a layered structure comprising
   (A) a backing layer,
   (B) a pressure sensitive adhesive scopolamine reservoir,
   (C) optionally a membrane controlling the scopolamine flux,
   (D) optionally an additional skin adhesive layer, and
   (E) a protective film,
   (F) optionally in said resevoir a composition to decrease saturation solubility of the scopolamine base therein.
   (G) optionally in said reservoir a composition to increase the solubility of
   the scopolamine base therein;
the layer B comprising a copolymer of an acrylic acid or methacrylic acid derivative monomer carrying a polar group, said copolymer itself or together with additives having a saturation solubility for the scopolamine base of 10–30%-wt., the scopolamine base being present therein in a concentration of 50 to 100% of its saturation solubility in the system.

2. A transdermal therapeutic system according to claim 1, wherein the scopolamine base is present in (B) in a concentration of 60 to 100% of its saturation solubility in the system.

3. A transdermal therapeutic system according to claim 1, wherein the polar group of the monomer comprises at least one of a carboxyl, hydroxyl and amino group.

4. A transdermal therapeutic system according the claim 1, which is a matrix system.

5. A transdermal therapeutic system according to claim 1, which is a membrane system.

6. A transdermal therapeutic system according to claim 5, comprising as the membrane (C) of such system a copolymer of ethylene and vinyl acetate.

7. A transdermal therapeutic system according to claim 6, wherein the copolymer comprises at least 4% by weight of vinyl acetate.

8. A transdermal therapeutic system according to claim 1, wherein (B) additionally contains a hydrocarbon to decrease the saturation solubility of the scopolamine base therein.

9. A transdermal therapeutic system according to claim 1, wherein (B) additionally contains dioctyl cyclohexane to decrease the saturation solubility of the scopolamine base therein.

10. A transdermal therapeutic system according to claim 1, wherein (B) additionally contains at least one fatty acid or alcohol to increase the solubility of the scopolamine base therein.

11. A transdermal therapeutic system according to claim 1, wherein (B) additionally contains at least one of oleic acid and oleyl alcohol to increase the solubility of the scopolamine base therein.

* * * * *